US00PP32250P2

(12) United States Plant Patent
Bak et al.

(10) Patent No.: US PP32,250 P2
(45) Date of Patent: Sep. 29, 2020

(54) ***VRIESEA* PLANT NAMED 'SHADE'**

(50) Latin Name: ***Vriesea* sp.**
Varietal Denomination: SHADE

(71) Applicant: Corn Bak B.V., Assendelft (NL)

(72) Inventors: Elly Bak, Rijsenhout (NL); Nicolaas Steur, Oude Niedorp (NL)

(73) Assignee: Corn Bak B.V. (NL)

( * ) Notice: Subject to any disclaimer, the term of this patent is extended or adjusted under 35 U.S.C. 154(b) by 0 days.

(21) Appl. No.: 16/602,006

(22) Filed: Jul. 18, 2019

(51) Int. Cl.
*A01H 5/02* (2018.01)
*A01H 6/22* (2018.01)

(52) U.S. Cl.
USPC ..... Plt./370

(58) Field of Classification Search
USPC ..... Plt./263.1, 370
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Vriesea* cultivar named 'SHADE' is disclosed, characterized by a compound, orange-red bipinnate spike inflorescence and light green foliage. The new variety is a *Vriesea*, typically produced as an indoor ornamental plant.

1 Drawing Sheet

Latin name of the genus and species: *Vriesea* sp.
Variety denomination: 'SHADE'.

BACKGROUND OF THE INVENTION

The present invention relates to a new and distinct cultivar of *Vriesea* plant, botanically known as *Vriesea*, hereinafter referred to by the cultivar name 'SHADE'. The genus of *Vriesea* belongs to the Bromeliaceae family. The new *Vriesea* cultivar is a product of a planned breeding program conducted by the inventors, Elly Bak and Nico D. M. Steur, in Assendelft, The Netherlands. The objective of the breeding program is to develop a new *Vriesea* variety with good growing habit and attractive inflorescence.

The new *Vriesea* cultivar 'SHADE' originated from a cross-made in a controlled breeding program by the inventors in 1994 in Assendelft, The Netherlands. The seed parent is an unpatented *Vriesea* selection designated '910209'. The pollen parent is an unpatented *Vriesea* selection designated '910234'. 'SHADE' was discovered and selected by the inventors in November of 1997, as a single flowering plant within the progeny of the stated cross in a controlled environment in Assendelft, The Netherlands.

Asexual reproduction of the new cultivar 'SHADE' performed by vegetative means by tissue culture was first performed in 2008, in Assendelft, The Netherlands. The first 'SHADE' plants propagated through the use of tissue culture flowered in 2012, in Assendelft, The Netherlands, and have demonstrated that the combination of characteristics as herein disclosed for the new cultivar are firmly fixed and retained through successive generations of asexual reproduction. The new cultivar reproduces true-to-type.

SUMMARY OF THE INVENTION

The cultivar 'SHADE' has not been observed under all possible environmental conditions. The phenotype may vary somewhat with variations in environment such as temperature, day length, and light intensity, without, however, any variance in genotype.

BRIEF DESCRIPTION OF THE INVENTION

The following traits have been repeatedly observed and are determined to be the unique characteristics of 'SHADE'. These characteristics in combination distinguish 'SHADE' as a new and distinct *Vriesea* cultivar:

1. Funnel form rosette.
2. Compound, orange-red bipinnate spike inflorescence.
3. About 3 ornamental orange-red bract-like branches below main inflorescence.
4. Light green foliage.

PARENT COMPARISON

Plants of the parents, '910209' and '910234' are no longer available to provide a botanical comparison with the new *Vriesea* cultivar 'SHADE'.

COMMERCIAL COMPARISON

'SHADE' is similar in most horticultural characteristics to the unpatented commercial variety *Vriesea* 'STYLE', U.S. Plant Pat. No. 18,176. However the new variety, 'SHADE' differs in the following:

1. The new variety has an orange inflorescence, while this comparator has a red inflorescence.

BRIEF DESCRIPTION OF THE PHOTOGRAPH

The accompanying drawing illustrates the overall appearance of the new *Vriesea* cultivar 'SHADE' showing the colors as true as is reasonably possible with colored reproductions of this type. Colors in the photograph may differ slightly from the color values cited in the detailed botanical description which accurately describes the color of 'SHADE'. The photograph shows a side perspective view of a typical potted flowering plant of 'SHADE' at about 18 months of age from potting size.

DETAILED BOTANICAL DESCRIPTION

'SHADE' has not been observed under all possible environmental conditions. The phenotype of the new cultivar may vary with variations in environment such as temperature, light intensity, day length, fertilizers and humidity without any change in the genotype of the plant. The afore mentioned photograph, together with the following observations, measurements and values describe the new *Vriesea* cultivar as grown in a greenhouse in Assendelft, The Netherlands, under conditions which closely approximate those generally used in commercial practice. Plants of 'SHADE' were grown in a greenhouse with day temperatures ranging from 20° C. to 28° C. and night temperatures ranging from 18° C. to 23° C. No artificial lighting or photoperiodic treatments were conducted, but plants of 'SHADE' are forced into flowering. The following fertilizer is added when growing plants of 'SHADE': 1 part nitrogen, 0.6 parts phosphor, 2 parts Kalium and 0.1 parts magnesium. Color references are made to The Royal Horticultural Society Colour Chart (R.H.S.) 2007, except where general colors of ordinary significance are used. Color values were taken under daylight conditions in a greenhouse in Assendelft, The Netherlands. The age of the plants of 'SHADE' described is about 18 months from potting size.

Botanical classification: *Vriesea* hybrid 'SHADE'.

PROPAGATION

Type of propagation typically used: Tissue culture.

PLANT

Growth habit: Funnel form rosette.
Height: Approximately: 40 cm.
Plant spread: Approximately: 55 cm.
Plant vigor: Good.
Flowering season: A fully grown plant can flower year-round, starting approximately 16 weeks after induction of natural light or trough flowering treatment.
Cold tolerance: Frost tender. Temperatures below 5° C. may damage plants.
Fragrance: None.
Root description: Densely branched, non-fibrous, non-fleshy, colored Greyed-orange; near RHS 165A.

FOLIAGE

Leaf:
- *Quantity*.—About 17.
- *Average length*.—35 cm.
- *Average width*.—3.5-4.5 cm.
- *Shape of blade*.—Broad and linear.
- *Apex*.—Abruptly acuminate.
- *Base*.—Strap-like around central axis.
- *Margin*.—Entire.
- *Texture of top surface*.—Smooth, glabrous.
- *Texture of bottom surface*.—Smooth, glabrous.
- *Color*.—Young foliage upper side: RHS Green 137B. Young foliage under side: RHS Green 137B. Mature foliage upper side: RHS Green 137B. Mature foliage under side: RHS Green 137B, flushed with RHS Greyed-Purple 187A.
- *Venation*.—Type: Parallel. Venation coloration: Indistinguishable from leaf blade.

Petiole: No petiole present.
Bract-like branches:
- *Quantity*.—About 3.
- *Length*.—About 12-14 cm.
- *Width*.—About 5 cm.
- *Color*.—RHS Orange-Red 34A.

Bracts:
- *Quantity of bracts on main spike*.—About 26.
- *Arrangement*.—Alternate.
- *Length*.—About 5 cm.
- *Width*.—About 2.5 cm.
- *Overall shape*.—Ovate.
- *Color*.—RHS Orange-Red 34A.

INFLORESCENCE

General description: 1 flower per floral bract, typical for the genus *Vriesea*; flowering is normally in progression from base to tip of scape.
- *Inflorescence height*.—Approximately 27 cm.
- *Inflorescence width*.—Approximately 13 cm.
- *Shape*.—Bipinnate spike (main spike about 20 cm in length and about 8 cm in width, side spike about 12-14 cm in length and about 5 cm in width).
- *Color*.—RHS Orange-Red 34A.

Corolla:
- *Form*.—Long and narrow, petals and sepals fused at the base around the ovary.
- *Number*.—About 28 depending on the size of the plant.

Petals:
- *Number*.—3 per flower.
- *Length*.—About 5 cm.
- *Width*.—About 0.5 cm.
- *Overall shape*.—Ligulate.
- *Apex shape*.—Obtuse.
- *Base shape*.—Fused.
- *Texture*.—Smooth.
- *Color*.—Upper surface: RHS Yellow 8A. Lower surface: RHS Yellow 8A.

Sepals:
- *Number*.—3 per flower.
- *Length*.—About 3 cm.
- *Width*.—About 1 cm.
- *Overall shape*.—Ligulate.
- *Apex shape*.—Acute.
- *Base shape*.—Fused.
- *Texture*.—Smooth.
- *Color*.—Translucent, Yellow, closest to RHS Yellow 4D.

REPRODUCTIVE ORGANS

Androecium:
- *Stamen*.—Number: 6 per flower. Length: About 4.4 cm. Diameter: About 0.1 cm. Color: Near RHS Yellow 4C.
- *Anther*.—Length: About 0.6 cm. Color: Near RHS Yellow 4A.
- *Pollen*.—Amount: Scant. Color: Yellow, not accurately measured with R.H.S. chart.

Gynoecium:

*Pistil*.—Number: 1 per flower. Length: About 5.5 cm.

*Stigma*.—Shape: 3-parted. Width: About 0.5 cm. Color: Yellow-green, RHS 154C.

*Style*.—Length: About 5 cm. Color: Near RHS Yellow 4C.

*Ovary*.—Shape: Conical. Length: About 0.5 cm. Diameter: About 0.3 cm. Color: Near RHS Yellow 4D.

OTHER CHARACTERISTICS

Disease resistance: Neither resistance nor susceptibility to the normal diseases and pests of *Vriesea* has been observed.

Temperature tolerance: Frost tender. Temperatures below 5° C. may damage plants.

Fruit/seed production: No fruits/seeds detected to date.

What is claimed is:

1. A new and distinct cultivar of *Vriesea* plant named 'SHADE' as herein illustrated and described.

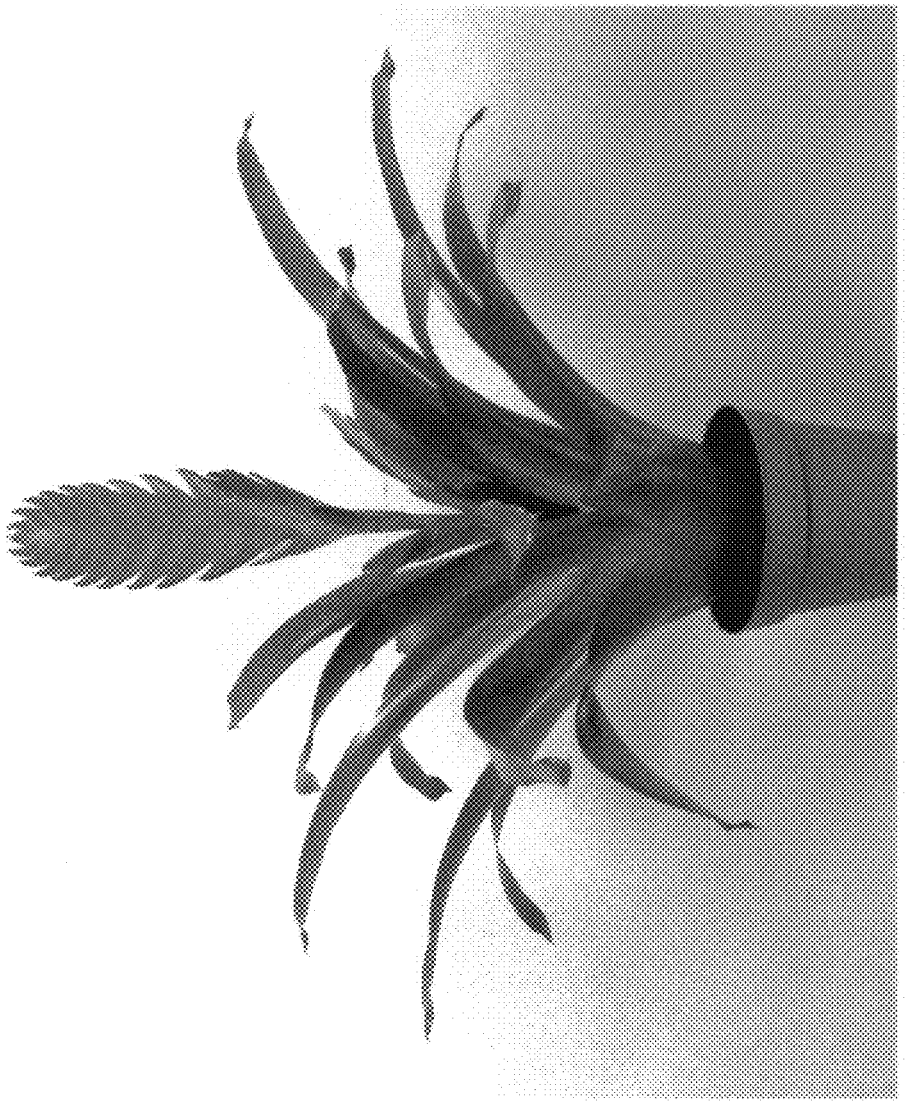

* * * * *